United States Patent
Hashimoto et al.

(10) Patent No.: US 8,900,211 B2
(45) Date of Patent: Dec. 2, 2014

(54) DISPOSABLE WEARING ARTICLE

(75) Inventors: Tatsuya Hashimoto, Kagawa (JP); Etsuko Kudo, Kagawa (JP); Toshifumi Otsubo, Kagawa (JP)

(73) Assignee: Unicharm Corporation, Ehime (JP)

( * ) Notice: Subject to any disclaimer, the term of this patent is extended or adjusted under 35 U.S.C. 154(b) by 86 days.

(21) Appl. No.: 13/698,103

(22) PCT Filed: Jun. 10, 2011

(86) PCT No.: PCT/JP2011/063333
§ 371 (c)(1),
(2), (4) Date: Nov. 15, 2012

(87) PCT Pub. No.: WO2011/155595
PCT Pub. Date: Dec. 15, 2011

(65) Prior Publication Data
US 2013/0060220 A1     Mar. 7, 2013

(30) Foreign Application Priority Data
Jun. 11, 2010   (JP) ................................ 2010-134559

(51) Int. Cl.
*A61F 13/15*     (2006.01)

(52) U.S. Cl.
USPC ............ 604/385.22; 604/385.24; 604/385.26; 604/385.3; 604/385.29

(58) Field of Classification Search
USPC ................. 604/367, 385.22, 385.24, 385.26, 604/385.3, 385.209, 385.29
See application file for complete search history.

(56) References Cited

U.S. PATENT DOCUMENTS

| 6,464,677 | B1 | 10/2002 | Noguchi et al. |
| 2002/0156444 | A1* | 10/2002 | Otsubo ..................... 604/385.3 |
| 2003/0031834 | A1 | 2/2003 | Ukegawa et al. |
| 2004/0111076 | A1* | 6/2004 | Sayama et al. ........... 604/385.13 |
| 2008/0124996 | A1 | 5/2008 | Hashimoto et al. |
| 2009/0035527 | A1 | 2/2009 | Kobayashi et al. |

FOREIGN PATENT DOCUMENTS

| JP | 3162854 A | 7/1991 |
| JP | 4166150 A | 6/1992 |
| JP | 4289201 A | 10/1992 |
| JP | 2001061885 A | 3/2001 |
| JP | 2007138374 A | 6/2007 |
| JP | 4070965 B2 | 4/2008 |
| JP | 2008148834 A | 7/2008 |
| WO | 2008066009 A1 | 6/2008 |

OTHER PUBLICATIONS

International Search Report and Written Opinion corresponding to PCT/JP2011/06333, dated Jul. 26, 2011.

* cited by examiner

*Primary Examiner* — Jacqueline F. Stephens
(74) *Attorney, Agent, or Firm* — Lowe Hauptman & Ham LLP

(57) ABSTRACT

The present invention provides a disposable wearing article adapted to inhibit sweating and an uncomfortable stuffiness. Front and rear waist regions of a disposable wearing article have inner surfaces thereof at least partially formed of elastic sheets. The elastic sheets are made of a mixture of elastic fibers and inelastic fibers and formed with ridges and grooves. The elastic sheets have a thickness in the ridges repetitively reduced and restored as the elastic sheets repeat elastic stretch and contraction in the waist circumferential direction.

12 Claims, 7 Drawing Sheets

DISPOSABLE WEARING ARTICLE

RELATED APPLICATIONS

The present application is a national Phase of International Application Number PCT/JP2011/063333, filed Jun. 10, 2011, and claims priority from Japanese Application Number 2010-134559, filed Jun. 11, 2010.

TECHNICAL FIELD

The present invention relates to disposable wearing articles such as disposable diapers.

BACKGROUND OF INVENTION

Wearing articles are known having front and rear waist regions and a crotch region wherein elastic sheets such as elastic nonwoven fabrics or plastic films are used in at least one of the front and rear waist regions. Wearing articles are also known in which a plurality of rubber yarns or threads or rubber ribbons are used instead of such elastic sheets. Such elastic materials are usually attached under tension in a waist circumferential direction to the waist region which is formed of inelastic sheets.

For example, JP 1991-162854A (PTL 1) discloses a disposable wearing article inclusive of an open-type diaper, a pants-type diaper and toilet-training pants including elastic top- and backsheets wherein an elastic barrier sheet formed of a plastic film is interposed between top- and backsheets.

In the disposable diaper disclosed in JP 1992-166150 A (PTL 2), a plurality of belt-like waist elastics are interposed between top- and backsheet in a region occupied by a bodily fluid absorbent panel. Waist elastics are attached under tension in the waist circumferential direction to the diaper so that, upon contraction of these elastics, a waist region is formed with gathers extended in the waist circumferential direction. The topsheet is formed of a nonwoven fabric made of, for example, polypropylene fibers and the backsheet is formed of a polyethylene film.

In disposable briefs disclosed in JP 1992-289201 A (PTL 3), a plurality of elastic ribbons is attached to the topsheet and/or the backsheet. Upon contraction of these elastic ribbons, the briefs are formed with a plurality of wrinkles.

CITATION LIST

Patent Literature

{PTL 1} JP 1991-162854 A
{PTL 2} JP 1992-166150 A
{PTL 3} JP 1992-289201 A

SUMMARY OF INVENTION

Technical Problem

In the wearing article having elastic sheets elastically contractible in a waist circumferential direction disposed so as to face a wearer's skin, these elastic sheets may come in close contact with the wearer's skin to ensure a desirable fit of the wearing article. However, the elastic sheets kept in close contact with the wearer's skin may cause the wearer to sweat and thereby may create an uncomfortable stuffiness.

Meanwhile, in the wearing article in which elastics such as rubber yarns or threads are used to be interposed between the top- and backsheets instead of the elastic sheet, a number of gathers each extending in the vertical direction are formed in the waist region upon contraction of these elastics in the waist circumferential direction. Considering that the top- and backsheets are usually attached together by bonding means such as hot melt adhesives, the top- and backsheets form the gathers of a single-layered structure in an integrated manner. Such gathers make it difficult to fold or roll up the wearing article in the direction orthogonal to the direction in which the gathers extend. In consequence, the user may feel a poor softness and/or poor flexibility of the wearing article when the user handles the article.

An object of the present invention is to overcome the above-mentioned problems occurring in the wearing articles provided in the waist regions with the elastics such as the elastic sheets or the rubber yarns or threads.

Solution to Problem

According to the present invention, there is provided a disposable wearing article including a front waist region, a rear waist region and a crotch region, each having an inner surface facing the wearer's skin and an outer surface facing the wearer's garment. The front and rear waist regions are elastically contractible in a waist circumferential direction. The inner surfaces of the front and rear waist regions are at least partially formed of elastically contractible elastic sheets.

The present invention further includes the following features:

the elastic sheets are formed of a mixture of elastically stretchable elastic fibers and inelastically stretchable inelastic fibers;

ridges and grooves being convex and concave with respect to the wearer's skin are formed of the elastic fibers and the inelastic fibers;

the ridges and the grooves extend in a vertical direction of the wearing article and arranged alternately in the waist circumferential direction; and the elastic sheets have a thickness in the ridges repetitively reduced and restored as the elastic sheets repeat elastic stretch and contraction in the waist circumferential direction.

According to one embodiment of the present invention, the wearing article includes a bodily fluid absorbent panel extending across the crotch region further into the front and rear waist regions and, in at least one of the front and rear waist regions, the elastic sheet covers an end of the panel from the inner side of the wearing article and extends in the waist circumferential direction.

According to another embodiment of the present invention, the outer surface of the elastic sheet is attached to an outer sheet at least partially defining the outer surface of the wearing article from an inner side of the wearing article, the outer sheet is formed of a nonwoven fabric made of inelastically stretchable fibers, and the outer sheet is formed with gathers undulating in the waist circumferential direction.

According to still another embodiment of the present invention, each of the elastic sheets is formed of a spun bonded nonwoven fabric having a mass per unit area in a range of 20 to 50 g/m$^2$, the elastic fibers include polyurethane filaments having a fineness in a range of 2 to 6 dtex, the inelastic fibers include at least one of polyolefin filaments, polyester filaments and polyamide filaments having a fineness in a range of 2 to 6 dtex, and the elastic fibers and the inelastic fibers are mixed at a mass ratio in a range of 40:60 to 60:40.

According to yet another embodiment of the present invention, the outer sheet includes the inelastic fibers in a crimped state.

According to further another embodiment of the present invention, the wearing article is of pants-type and respective lateral edges of the front and rear waist regions are joined together at a series of joining portions extending along the lateral edges, the joining portions each has an area of 1 mm² or less.

According to still another embodiment of the present invention, the elastic sheets are rectangularly configured extending in a transverse direction of the article and a dimension of the elastic sheets in a vertical direction of the article is less than a dimension of each of the front and rear waist regions in the vertical direction, wherein the elastic sheets are positioned in generally middle zones of the front and rear waist regions in the vertical direction.

Advantageous Effects of Invention

In the disposable wearing article according to the present invention, the inner surface facing the wearer's skin is formed at least partially of the elastic sheets which are formed with ridges being convex with respect to the wearer's skin and the grooves being concave with respect to the wearer's skin. These ridges and grooves extend in the vertical direction of the wearing article and are arranged alternately in the waist circumferential direction. During use of the wearing article, the ridges of the elastic sheets are put in contact with the wearer's skin, and a plurality of void spaces are defined between the respective grooves and the wearer's skin. The presence of these void spaces allows air and moisture vapor to move and inhibits sweating and an uncomfortable stuffiness. When the elastic sheets for elastically contracting the waist regions are attached to the outer sheet of the wearing article, a quantity of hot melt adhesives can be reduced in comparison to where the rubber yarns or threads are secured to the outer sheet for elastically contracting the waist regions, and thereby the softness and flexibility of the wearing article are unlikely to be deteriorated by hot melt adhesives.

DESCRIPTION OF EMBODIMENTS

Details of a disposable wearing article will be more fully understood from the description given hereunder of a disposable pants-type diaper as a typical example thereof with reference to the accompanying drawings.

Figure 1:
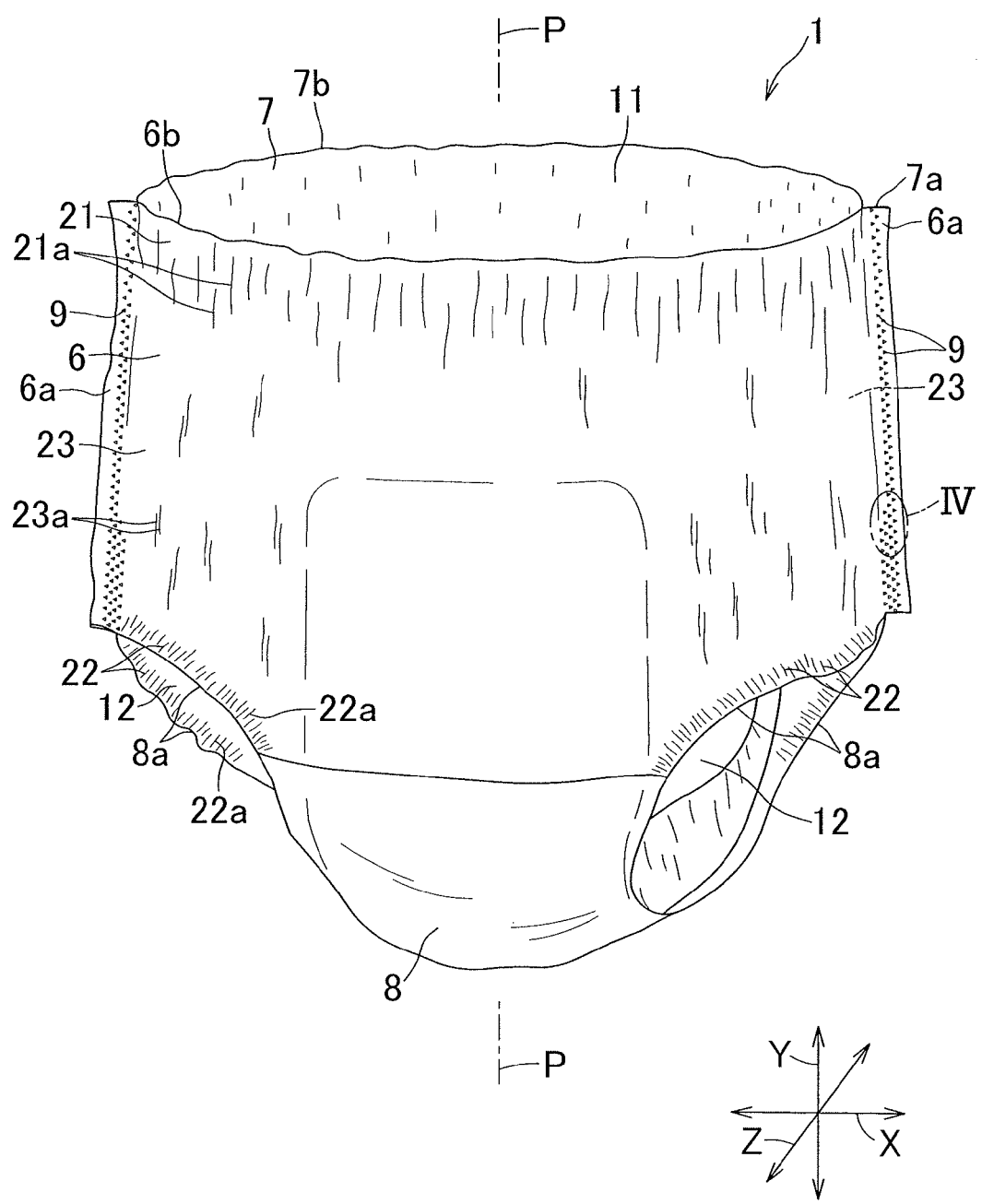
FIG. 1 is a perspective view of a pants-type diaper as an example of a disposable wearing article.

FIG. 1 is a perspective view of a disposable pants-type diaper 1. The diaper 1 has a front waist region 6, a rear waist region 7 and a crotch region 8 extending in a front-back direction Z between the front and rear waist regions 6, 7. Respective lateral edges 6a, 7a of the front and rear waist regions 6, 7 are joined together at a series of joining portions 9 extending in a vertical direction Y of the diaper 1 and thereupon a waist-opening 11 and a pair of leg-openings 12 are formed. An edge 6b of the front waist region 6 and an edge 7b of the rear waist region 7 cooperating with each other to define the waist-opening 11 are formed with first elasticized zones 21 including a plurality of first gathers 21a extending in the vertical direction Y. In the crotch region 8, opposite edges 8a defining the respective leg-openings 12 are formed with second elasticized zones 22 at least partially including second gathers 22a obliquely extending in the vertical direction Y. Respective middle zones of the front and rear waist regions 6, 7 as viewed in the vertical direction Y are formed with third elasticized zones 23 including a plurality of third gathers 23a extending in the vertical direction Y. Referring to FIG. 1, double-headed arrows X, Y and Z respectively denote a transverse direction, the vertical direction and the front-back direction of the diaper 1.

Figure 2:
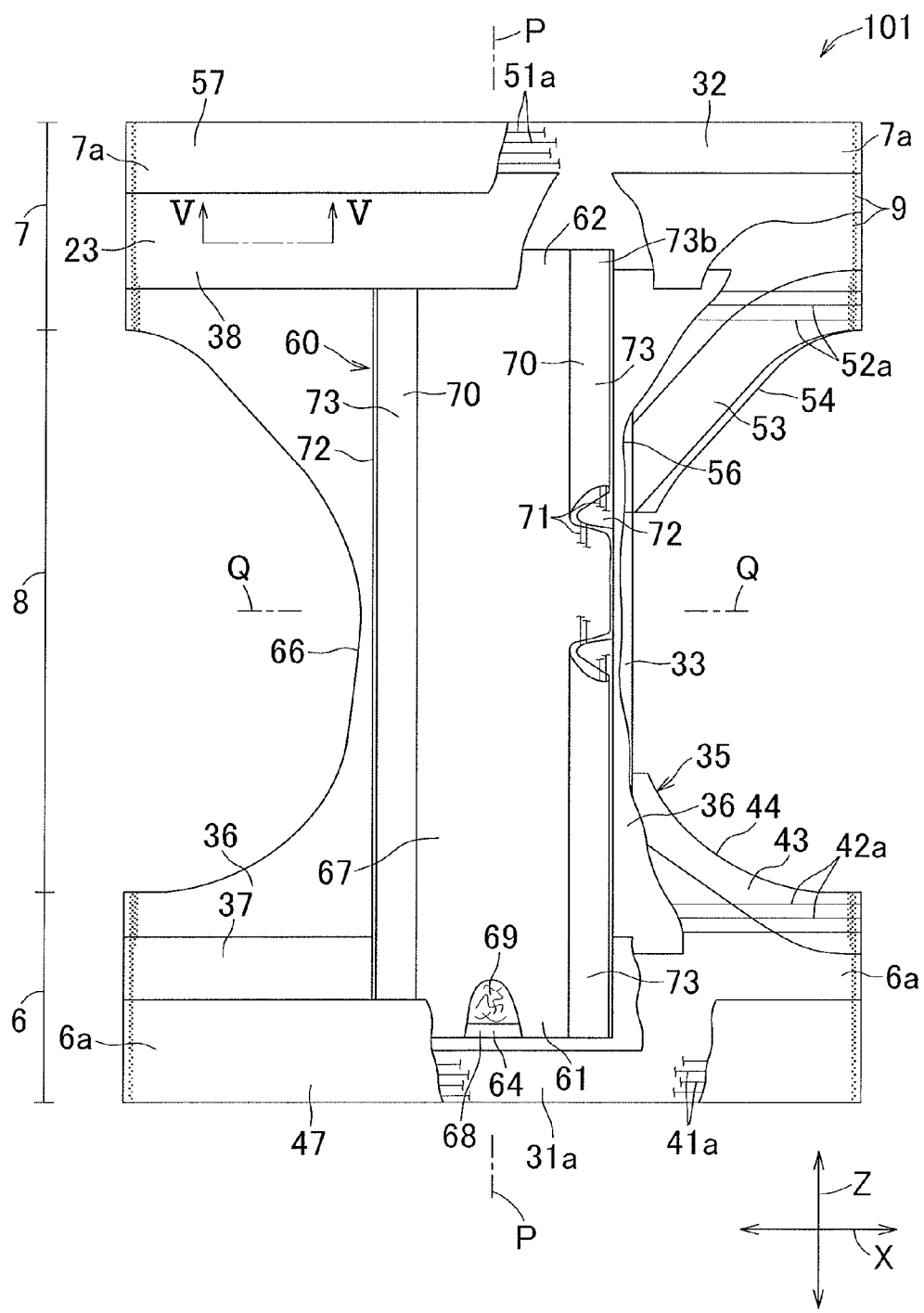
FIG. 2 is a partially cutaway plan view showing the diaper having been flatly developed.
Figure 3:
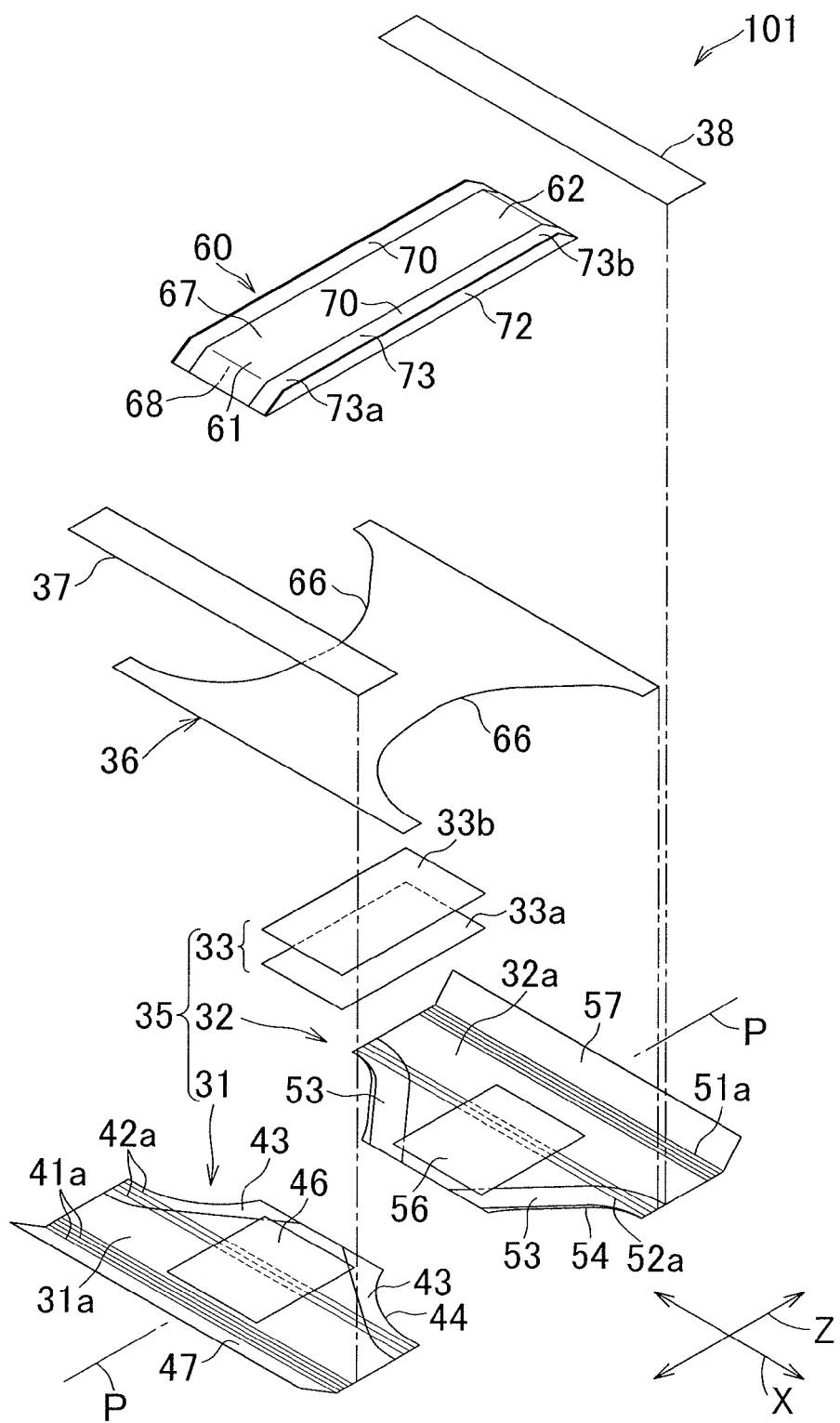
FIG. 3 is an exploded perspective view of the flatly developed diaper.

FIG. 2 is a partially cutaway plan view showing the diaper 1 flatly developed after the front and rear waist regions 6, 7 having been peeled off from each other along the seam arrays 9 and stretched in the transverse direction X as well as in the front-back direction Z so that the first through third gathers 21a through 23a may substantially disappear and FIG. 3 is an exploded perspective view of such developed diaper 101. The developed diaper 101 is shaped symmetrically about first center line P-P bisecting a dimension thereof in the transverse direction X. The developed diaper 101 shown in FIG. 2 may be folded along second center line Q-Q bisecting a dimension thereof in the front-back direction Z and the lateral edges 6a of the front waist region 6 may be joined to the lateral edges 7a of the rear waist region 7 to construct the diaper 1 of pants-type.

As shown in FIGS. 2 and 3, the developed diaper 101 includes a front panel 31 defining the front waist region 6 and part of the crotch region 8, a rear panel 32 defining the rear waist region 7 and part of the crotch region 8 and an intermediate panel 33 adapted to join these front and rear panels 31, 32 in the crotch region 8. These three panels 31, 32, 33 may be integrated to form a chassis 35 in the developed diaper 101 and the diaper 1. To an inner surface of the chassis 35, more specifically, to an upper surface of the chassis 35 as viewed in FIG. 3, an intermediate sheet 36 extending in respective parts of the front and rear waist regions 6, 7 and in the crotch region 8 is attached with hot melt adhesives (not shown). To an inner surface of the front panel 31 in the chassis 35, a front elastic sheet 37 adapted to be elastically contractible in the transverse direction X is attached under tension with hot melt adhesives (not shown) intermittently coated in the transverse direction X and the front-back direction Z, at least in the transverse direction X. The front elastic sheet 37 partially overlaps the intermediate sheet 36. A bodily fluid absorbent panel 60 and a rear elastic sheet 38 are attached with hot melt adhesives (not shown) to the inner surface of the chassis 35 to which the front sheet 37 has been attached. The bodily fluid absorbent panel 60 is attached to the chassis 35 so as to extend across the crotch region 8 of the diaper 1 further into part of the front waist region 6 and part of the rear waist region 7. Part of the rear sheet 38 is attached to the chassis 35 from above the developed diaper 101 of FIG. 3, in other words, from the inner side of the developed diaper 101 so that the rear elastic sheet 38 may partially overlap the bodily fluid absorbent panel 60 as shown in FIG. 2.

As shown in FIGS. 2 and 3, the elastic sheet 37, 38 are configured in a rectangular shape extending in the transverse direction X and a dimension of the elastic sheets 37, 38 in the vertical direction Y is less than a dimension of each of the front and rear waist regions 6, 7 in the vertical direction Y, wherein the elastic sheets 37, 38 are positioned in generally middle zones of the front and rear waist regions 6, 7 in the vertical direction Y.

In the developed diaper 101 formed as has been described above, the front panel 31 of the chassis 35 includes a sheet member 31a defining at least partially the outer surface of the diaper 1. A plurality of thread, string or strand first front elastics 41a extending in the waist circumferential direction, in other words, in the transverse direction X as viewed in FIGS. 2 and 3 and a plurality of thread, string or strand second front elastics 42a are secured under tension to the inner surface of the sheet member 31a with hot melt adhesives (not shown). An elongate front leg elastic 43 is secured under tension to each of zones 44 of the sheet member 31a defining the respective edges 8a (See FIG. 1) of the leg-openings 12 of the diaper 1 with hot melt adhesives (not shown). Of the respective front leg elastics 43 and the second front elastics 42 partially overlapping one another, the front leg elastics 43 are secured under tension to the sheet member 31a and the second front elastics 42 are secured under tension to the respective front leg elastics 43. A front leakage-barrier sheet 46 formed of a liquid-impervious plastic film is attached to the inner surface of the sheet member 31a with hot melt adhesives (not shown) so as to overlap the second front elastics 42 and the front leg elastics 43. An end 47 of the sheet member 31a extending in the transverse direction X may be folded inwardly of the diaper 1 to cover the first front elastics 41a and a front end 61 of the bodily fluid absorbent panel 60 and attached to respective zones facing this folded end 47 with hot melt adhesives (not shown).

The rear panel 32 constituting the chassis 35 includes a sheet member 32a defining at least a part of the outer surface of the diaper 1. This sheet member 32a is provided on its inner surface with a plurality of first thread, string or strand rear elastics 51a and a plurality of second thread, string or strand rear elastics 52a both extending in the transverse direction X secured under tension thereto with hot melt adhesives (not shown). An elongate rear leg elastic 53 is attached under tension to each of zones 54 of the sheet member 32a defining the respective edges 8a of the leg-openings 12 of the diaper 1 with hot melt adhesives (not shown). Of the respective rear leg elastics 53 and the second rear elastics 52a partially overlapping one another, the rear leg elastics 53 are secured under tension to the sheet member 32a and the second rear elastics 52a are attached under tension to the respective rear leg elastics 53. A rear leakage-barrier sheet 56 formed of a liquid-impervious plastic film is attached to the inner surface of the sheet member 32a with hot melt adhesives (not shown) so as to overlap the second rear elastics 52a and the rear leg elastics 53. An end 57 of the sheet member 32a extending in the transverse direction X may be folded inwardly of the diaper 1 to cover the first rear elastics 51a and a rear end 62 of the bodily fluid absorbent panel 60 and attached to respective zones facing this folded end 57 with hot melt adhesives (not shown).

In these front and rear panels 31, 32, the sheet members 31a, 32a may be formed of a nonwoven fabric such as a spun bonded nonwoven fabric or a melt bonded nonwoven fabric, and such a nonwoven fabric is preferably formed of a thermally bonded nonwoven fabric containing thermally crimped conjugate fibers each having a length in a range of 30 to 70 mm so that the crimped conjugate fibers may provide the outer surface of the diaper 1 with a comfortable soft texture. The first and second front elastics 41a, 42a as well as the first and second rear elastics 51a, 52a may be coated on the surfaces thereof with hot melt adhesives in an amount in a range of 10 to 17 g/m$^2$ and may be secured to the sheet members 31a, 32a, respectively. The front leg elastics 43 and the rear leg elastic 53 may be formed of the same material as the material of the front elastic sheet 37 and the rear elastic sheet 38 and also may be formed of material having a different elastic modulus from that of the material of the front elastic sheet 37 and the rear elastic sheet 38. sheets The preferred front and rear elastic sheets 37, 38 may have a width in a range of 15 to 30 mm as viewed in the front-back direction Z in FIGS. 2 and 3, and the sheet members 31a, 32a and the intermediate sheet 36 may be respectively coated with hot melt adhesives in an amount in a range of 2 to 5 g/m$^2$ with which the front and rear elastic sheets 37, 38 may be attached to them. A pattern in which hot melt adhesives are coated to the sheet members 31a, 32a and the intermediate sheet 36 may be appropriately selected from various patterns such as a dot-pattern and an omega-pattern. In the sheet members 31a, 32a containing thermally crimped conjugate fibers, these sheet members 31a, 32a may be debossed under heating to form a plurality of intermittently arranged spot-like sealed zones and thereby to stabilize texture of the sheet members 31a, 32a.

A central panel 33 constituting the chassis 35 includes an outer sheet 33a formed of a nonwoven fabric made of thermoplastic synthetic fibers and an inner sheet 33b formed of a liquid-impervious plastic film wherein these inner and outer sheets 33a, 33b are attached to each other with hot melt adhesives (not shown). The outer sheet 33a is attached to respective inner surfaces of the front and rear panels 31, 32 with hot melt adhesives (not shown).

The intermediate sheet 36 in the developed diaper 101 has lateral edges 66 which are convexly curved toward the first center line P-P and respectively conform with the zones 44 of the front panel 31 and the zones 54 of the rear panel 32 to define the peripheral edges 8a of the leg-openings 12 (See FIG. 1) of the diaper 1 as the intermediate sheet 36 is placed upon the chassis 35. Such intermediate sheet 36 may be formed of a nonwoven fabric made of thermoplastic synthetic fibers or a plastic film. The preferred intermediate sheet 36 is water-repellent and/or liquid-impervious.

Figure 5:
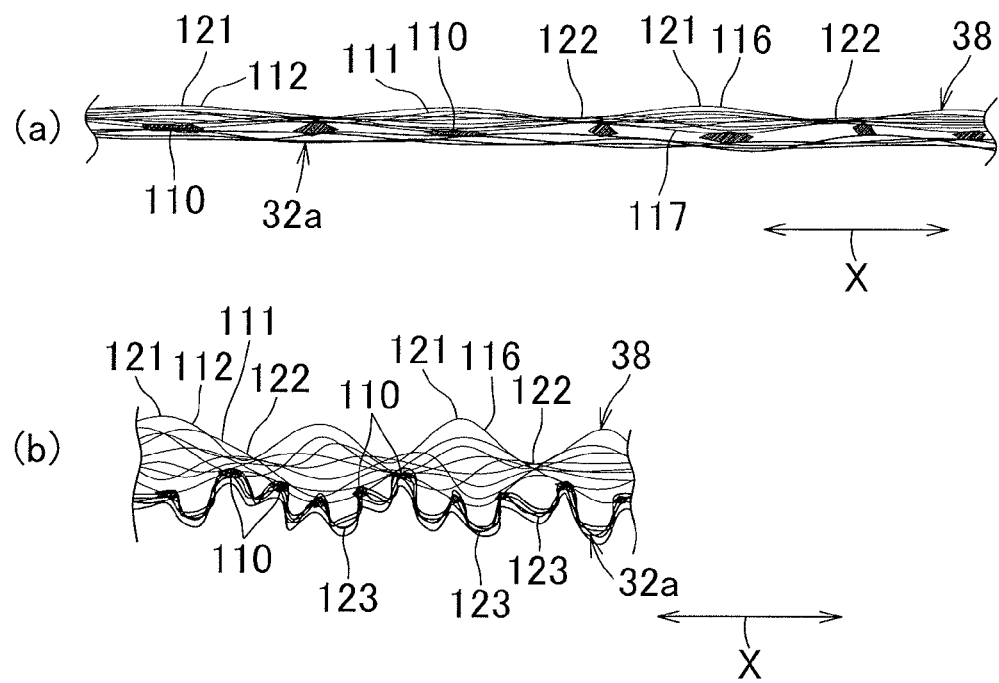
FIG. 5($a$) is a schematic diagram illustrating a cross-section taken along line V-V in FIG. 2 and FIG. 5($b$) is showing FIG. 5($a$) in a contracted state.

The front elastic sheet 37 and the rear elastic sheet 38 in the developed diaper 101 are respectively formed of nonwoven fabric pieces each including a mixture of filaments 111 (See FIG. 5) of elastically contractible elastic fibers and filaments 112 (See FIG. 5) of inelastically stretchable elastic fibers wherein the presence of the filaments 111 allows these front and rear elastic sheets 37, 38 to be elastically contracted in the transverse direction X. These sheets 37, 38 are attached under tension in the transverse direction X to the chassis 35 and the bodily fluid absorbent panel 60 with which those sheets 37, 38 overlap. Referring to FIG. 2, the front elastic sheet 37 is used to be interposed between the chassis 35 and the bodily fluid absorbent panel 60 and the rear elastic sheet 38 is used to cover the rear end 62 of the bodily fluid absorbent panel 60 from the inner side of the diaper 1. However, it is possible to exploit the developed diaper 101 according to the present invention in such a manner that the sheets 37, 38 are interposed between the chassis 35 and the bodily fluid absorbent panel 60 or the sheets 37, 38 cover the front and rear ends 61, 62 of the bodily fluid absorbent panel 60, respectively.

The bodily fluid absorbent panel 60 in the developed diaper 101 includes a liquid-pervious inner sheet 67, a water-repellent, more preferably water-repellent and liquid-impervious outer sheet 68 and a bodily fluid absorbent core 69 interposed between the inner and outer sheets 67, 68 wherein the core 69 may include an aggregate of bodily fluid absorbent materials, for example, fluff wood pulp and/or super-absorbent polymer particles or such aggregate wrapped with tissue paper. The bodily fluid absorbent panel 60 is formed along its lateral edges with containment barriers 70 extending in the front-back direction Z. Each of the containment barriers 70 is formed by folding back the water-repellent, more preferably water-repellent and liquid-impervious sheet 68 onto the sheet 67 and securing thread, string or strand elastics 71 under tension in the front-back direction Z between the sheets 67, 68 overlapping each other. Each of the containment barriers 70 has a proximal edge 72 and a distal edge 73 wherein the proximal edge 72 is affixed to the bodily fluid absorbent panel 60 over its full length in the front-back direction Z and the distal edge 73 has only its opposite end portions 73a, 73b in the front-back direction Z which overlap with the associated portions of the containment barrier 70 and affixed together with these portions to the bodily fluid absorbent panel 60. When the diaper 1 is put on the wearer's body and the crotch region 8 is bowed in a U-shape in the front-back direction Z, the elastics 71 contract and thereupon the distal edges 73 rise up on the inner surface of the bodily fluid absorbent panel 60. In this way, the three-dimensional containment barriers which are well known in the technical field of disposable diapers are obtained. The term "affixed" used herein with respect to the bodily fluid absorbent panel 60 and the containment barriers 70 means bonding of the associated members with hot melt adhesives.

Figure 4:
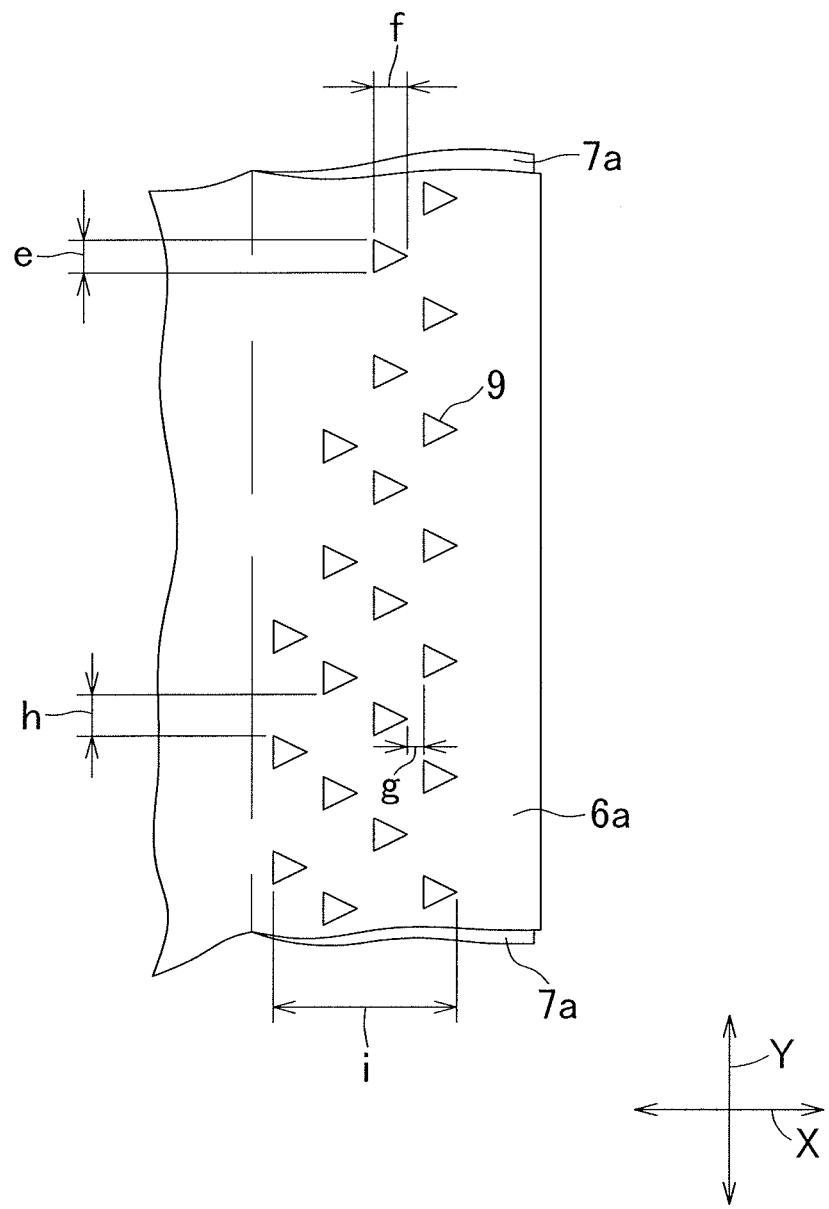
FIG. 4 is a diagram illustrating an encircled region IV in FIG. 1.

FIG. 4 is a scale-enlarged diagram of an encircled zone IV in FIG. 1 in an enlarged scale to illustrate an embodiment of the joining portions 9 arranged in a dot-pattern serving at which the lateral edge 6a of the front waist region 6 is joined to the associated lateral edge 7a of the rear waist region 7. The respective joining portions 9 are formed by pressing ultrasonic seam welder's horns against these lateral edges 6a, 7a. In each of these substantially triangular joining portions 9, a length dimension e of the base as well as a height dimension f is in a range of 0.7 to 1.2 mm, more preferably, the individual joining portion 9 preferably has an area of 1 mm$^2$ or less. A distance dimension g between adjacent joining portions 9 in the transverse direction X is in a range of 0.3 to 0.7 mm, a distance dimension h between adjacent joining portions 9 in the vertical direction Y is in a range of 0.7 to 3.7 mm and a width dimension i of a zone formed with the joining portions 9 in the transverse direction X is in a range of 4 to 8 mm. The joining portions 9 each having an area preferably equal to or less than 1 mm$^2$ may be distributed in a dot-pattern along the lateral edges 6a and the lateral edges 7a to solve the problem that the presence of the joining portions 9 might make the lateral edges 6a, 7a unacceptably stiff. In consequence, the diaper 1 as a whole can be easily folded in the vertical direction Y or rolled up.

FIG. 5(a) is a schematic diagram illustrating a cross-section taken along line V-V in FIG. 2 and FIG. 5(b) is showing FIG. 5(a) in a contracted state. The line V-V extends in the third elasticized zone 23 in the rear waist region 7.

In the rear panel 32, the sheet member 32a and the rear elastic sheet 38 are attached to each other with hot melt adhesives 110 as illustrated in FIG. 5(a) which is applied to the sheet member 32a in an amount of 2 to 5 g/m$^2$ intermittently in the transverse direction X and the front-back direction Z, at least in the transverse direction X in FIG. 2. The rear elastic sheet 38 is formed of a nonwoven fabric containing a mixture of the elastically stretchable filaments 111 and the inelastically stretchable filaments 112 wherein these filaments 111, 112 are fusion-bonded at some of crossover portions thereof. While the rear elastic sheet 38 is in a state of contraction in the transverse direction X in the third elasticized zone 23 in FIG. 1, in FIG. 5(a), the elastic sheet 38 is in a stretched state in the transverse direction X at a stretch ratio of 1.5 to 3.0. Such rear elastic sheet 38 has an inner surface 116 facing the wearer's skin (not shown) and an outer surface 117 facing the wearer's garment.

Referring to FIG. 5(a), the inner surface 116 is substantially smooth or gently undulates. The outer surface 117 is attached to the sheet member 32a. The sheet member 32a is formed of a nonwoven fabric such as a spun bonded nonwoven fabric and a melt bonded nonwoven fabric made of thermoplastic synthetic fibers 113 in the form of filaments or staples and substantially neither elastically stretchable nor elastically contractible.

FIG. 5(b) shows respective cross-sections of the rear elastic sheet 38 and the sheet member 32a in which the rear waist region 7 has been freed from the force acting to stretch it and the rear elastic sheet 38 is in an elastically contracted state in the transverse direction X. The states of the rear elastic sheet 38 and the sheet member 32a illustrated in FIG. 5b correspond to the states of the rear elastic sheet 38 and the sheet member 32a in the third elasticized zone 23 illustrated in FIG. 1. On the inner surface 116 of the rear elastic sheet 38 having been contracted, ridges 121 which are convex toward the wearer's skin and grooves 122 which are concave with respect to the wearer's skin appear alternately in the transverse direction X. When the rear elastic sheet 38 changes from the state of FIG. 5(a) to the state of FIG. 5(b), the filament 111 elastically contract to shorten its length but the filament 112 does not contract but sags. The ridge 121 is a zone defined by bundle of these filaments 112 and is sufficiently supple to be easily deformed merely by light-touching with one's fingertips. The ridges 121 and the grooves 122 extend in the front-back direction Z in the developed diaper 101 shown in FIG. 2 but extend in the vertical direction Y in the diaper 1 shown in FIG. 1. It should be appreciated that the ridges 121 and the grooves 122 may extend over the full length of the rear elastic sheet 38 in the front-back direction Z in FIG. 2 or may disappear on the way of this full length. Even when the ridges 121 and the grooves 122 extend over the full length of the rear elastic sheet 38 in the front-back direction Z in FIG. 2, the ridges 121 and the grooves 122 may be rectilinear or curved. The ridges 121 formed in the fashion as has been described above scarcely has a role to enforce a stiffness of the rear elastic sheet 38 and is preferable in consideration of the flexibility of the rear elasticized sheet 38.

The sheet member 32a attached to the rear elastic sheet 38 is deformed under contraction of the rear elastic sheet 38 so that the irregular undulation appears in the transverse direction X to form gathers 123. The gathers 123 are of a single-layered structure formed only by the sheet member 32a and not of a two-layered structure and therefore the gathers 123 are sufficiently flexible to be easily deformed merely by light-touching with one's fingertips. Such gathers 123 appear as the third gathers 23 in the rear waist region 7 of the diaper 1 as seen in FIG. 1. Specifically, in the rear panel 32, a zone in which the rear elastic sheet 38 is present defines the third elasticized zone 23 as shown in FIG. 1. The first gathers 21 in the rear waist region 7 of the diaper 1 are formed primarily by contraction of the first rear elastics 51a, and a zone in which the first rear elastics 51a are present and the vicinity thereof define the first elasticized zone 21 of the rear waist region 7. The second gathers 22 are formed primarily by contraction of the rear leg elastics 53 and a region in which the rear leg elastics 53 are present and the vicinity thereof define the second elasticized zones 22.

In the developed diaper 101 shown in FIG. 2, the front elastic sheet 37 and the sheet member 31a in the front panel 31 overlapping each other correspond to the rear elastic sheet 38 and the sheet member 32a so that, in the diaper 1 of FIG. 1 in which the front elastic sheet 37 in a contracted state, ridges and grooves substantially similar to the ridges 121 and the grooves 122 in FIG. 5(b) appear on the inner surface of the front elastic sheet 37 and the third gathers 23 (See FIG. 1) irregularly undulating in the waist circumferential direction appear on the outer surface of the sheet member 31a. Specifically, in the front panel 31, a zone in which the front elastic sheet 37 is present defines the third elasticized zone 23 of the front waist region 6 in FIG. 1. The first gathers 21 in the front waist region 6 of the diaper 1 are formed primarily by contraction of the first front elastics 41a and a region in which the first front elastics 41a are present and the vicinity thereof define the first elasticized zones 21. The second gathers 22 in the vicinity of the front waist region 6 of the diaper 1 are formed primarily by contraction of the front leg elastics 43 and, a region in which the front leg elastic 43 and the vicinity thereof define the second elasticized zones 22.

With such an arrangement of the front elastic sheet 37 and the rear elastic sheet 38 as illustrated above, when the ridges 121 come in contact with the wearer's skin during use of the wearing article, void spaces are ensured between the grooves 122 and the wearer's skin so that air and moisture vapor may move through these void spaces to inhibit sweating and stuffiness. Particularly when the rear elastic sheet 38 lies on the inner side of the bodily fluid absorbent panel 60 in the rear waist region 7 as illustrated in FIG. 2 as an example, the bodily fluid absorbent panel 60 containing moisture should not come in close contact with the wearer's skin in the rear waist region 7. In addition, the grooves 121 ensure the void spaces between the wearer's skin and the rear elastic sheet 38 allowing air and moisture vapor to move along them so as to effectively prevent the uncomfortable stuffiness.

In the wearing article according to the present invention described herein in the form of the diaper 1 as an embodiment, the joining portions 9 at which the lateral edges 6a, 7a of the front and rear waist regions 6, 7 are exploited in the fashion as illustrated in FIG. 4 and thereby it is possible to solve the problem that the presence of the joining portions 9 might make the lateral edges 6a, 7a undesirably stiff and make it difficult for these lateral edges 6a, 7a to be deformed. In consequence, it is possible to make the wearing article soft and flexible.

In the diaper 1, in order to define the respective third elasticized zones 23 in the front and rear waist regions 6, 7, the front elastic sheet 37 and the rear elastic sheet 38 each formed of a nonwoven fabric and having a relatively large dimension (width) in the vertical direction Y of FIG. 1 instead of using a plurality of rubber yarns or threads as conventionally used. These elastic sheets 37, 38 serve also as liners for the sheet member 31a and the sheet member 32. Compared to the diaper of prior art in which a plurality of rubber yarns or threads are interposed between a pair of sheets, a quantity of hot melt adhesives used in the waist regions can be reduced and thereby the waist regions are become stiff due to hot melt adhesives used in these waist regions.

The gathers 123 formed on the outer surfaces of the front and rear waist regions 6, 7 are respectively of a single-layered structure and contribute to make the front and rear waist regions 6, 7 soft and flexible.

The respective inner surfaces of the front and rear waist regions 6, 7 on which the front elastic sheet 37 and the rear elastic sheet 38 are used can be made to be soft and flexible by the presence of the ridges 121 on these two sheets 37, 38 and the respective outer surfaces of the front and rear waist regions 6, 7 can be made to be soft and flexible when crimped fibers are used for the sheet members 31a, 32a.

Figure 6:
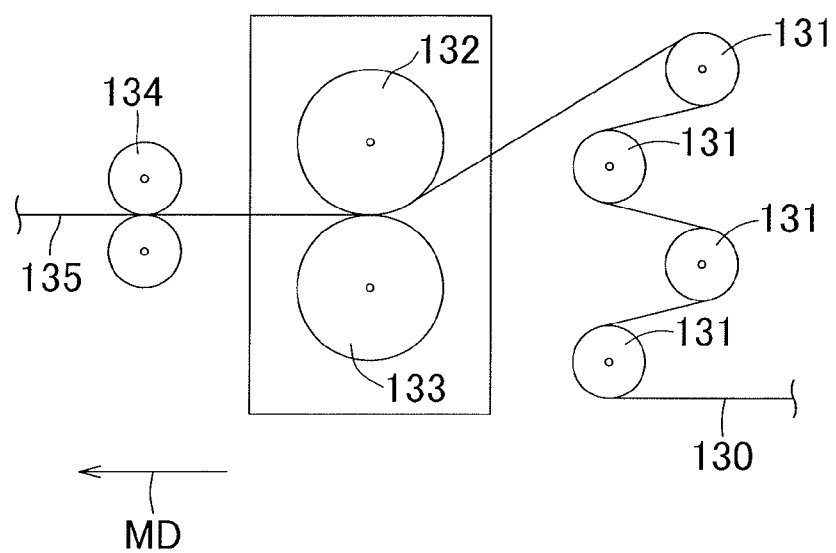
FIG. 6 is a diagram partially illustrating a process for producing an elastic web.
Figure 7:
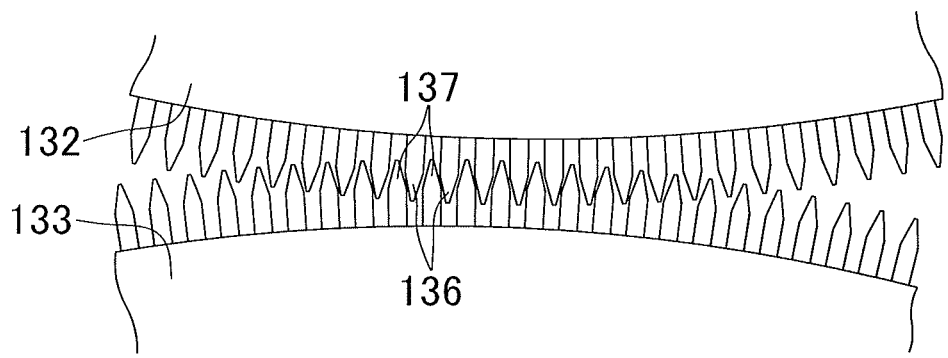
FIG. 7 is a side view of draft rolls.
Figure 8:
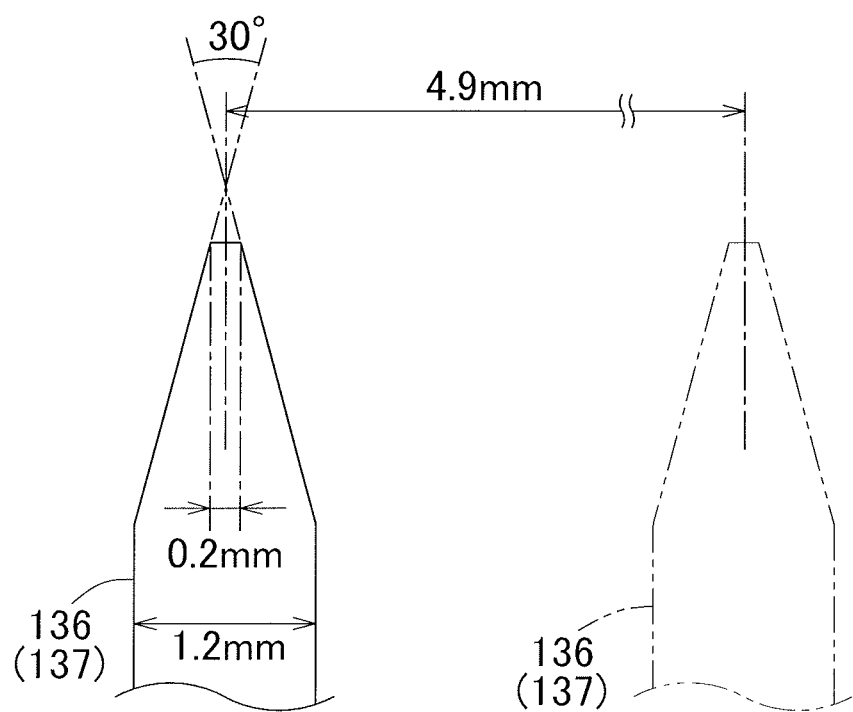
FIG. 8 is a diagram illustrating configuration of the draft rolls' teeth.

FIG. 6 is a diagram partially illustrating a process for producing an elastic web 135 used as the front elastic sheet 37 and the rear elastic sheet 38, FIG. 7 is a side view of partially illustrating gear-type rolls 132, 133 and FIG. 8 is a partially scale-enlarged diagram illustrating the gear-type roll 132 of FIG. 7. A preheated web 130 including a mixture of filaments 111 of elastic fibers such as polyurethane fibers and filaments 112 of inelastic fibers containing at least one of polyolefin fibers, polyester fibers and polyamide fibers is fed from the right hand as viewed in the right hand of FIG. 6 toward the downstream in a machine direction MD and guided by a plurality of guide rolls 131. The term "elastic fiber" used herein with respect to the web 130 means one or more fibers having a length of $L_0$ at a room temperature having been stretched to the length of $2 L_0$ and freed from the stretching force one minute after to contract to a length of $1.1 L_0$. The term "inelastic fiber" used herein with respect to the web 130 means one or more filaments having a length of $L_1$ at a room temperature having been stretched to the length of $2 L_1$ and freed from the stretching force one minute after to contract to a length of $1.7 L_1$ or longer. The web 130 having guided by the guide rolls 131 is now fed into a nip between a pair of the gear-type rolls 132, 133 which have been preheated at a predetermined temperature and stretched at a stretch ratio, for example, in a range of 1.5 to 3.0.

The web stretched in this manner leaves the gear-type rolls 132, 133 and, in a course of being fed to the feed rolls 134 or in the subsequent course, restores it initial dimension or it substantial dimension and is fed to a process of making the diaper 1 (not shown). While the filaments 111 in the web 130 elastically contract to their substantially initial dimension after having been stretched, the filaments 112 of inelastic fibers are inelastically stretched and permanently deformed to be lengthened and to form the ridges 121 as illustrated in FIG. 5(b). Such elastic web 135 under the state elastically stretched at a predetermined ratio in the machine direction MD is intermittently attached under tension at a predetermined ratio in the machine direction MD to the fibrous webs for the sheet members 31a, 32a.

The paired gear-type rolls 132, 133 shown in FIG. 6 are the same in size as well as in shape and respectively formed on peripheral surfaces with upper teeth 136 and lower teeth 137 at regular pitches in the circumferential direction so as to be precisely engaged one with another. The web 130 fed between the adjacent upper and lower teeth 136, 137 is stretched primarily in segments extending between the apices of the upper teeth 136 and the apices of the lower teeth 137 and substantially not stretched in points at which the apices of the upper teeth 136 come in contact with the apices of the lower teeth 137 so as to form the grooves 122 as illustrated in FIG. 5(b).

In FIG. 8, specific dimensions of respective regions in the upper teeth 136 and the lower teeth 137 are indicated as an example. In this specific example, a depth of engagement between the upper teeth 136 and the lower teeth 137 depends on a predetermined stretch ratio of the web 130 and, for example, if it is desired to stretch the web 130 at a ratio in a range of 2.5 to 3.0, the depth of engagement may be set to about 6 mm.

In the process illustrated in FIG. 6, the web 130 includes, for example, the filaments 111 of polyurethane fibers and the filaments 112 of polypropylene fibers both having a fineness in a range of 2.5 to 6 dtex mixed together at a mass ratio in a range of 40:60 to 60:40 so as to have a mass per unit area in a range of 20 to 50 g/m². This web 130 is preheated to about 55° C. and then fed to the gear-type rolls 132, 133.

Figure 9:
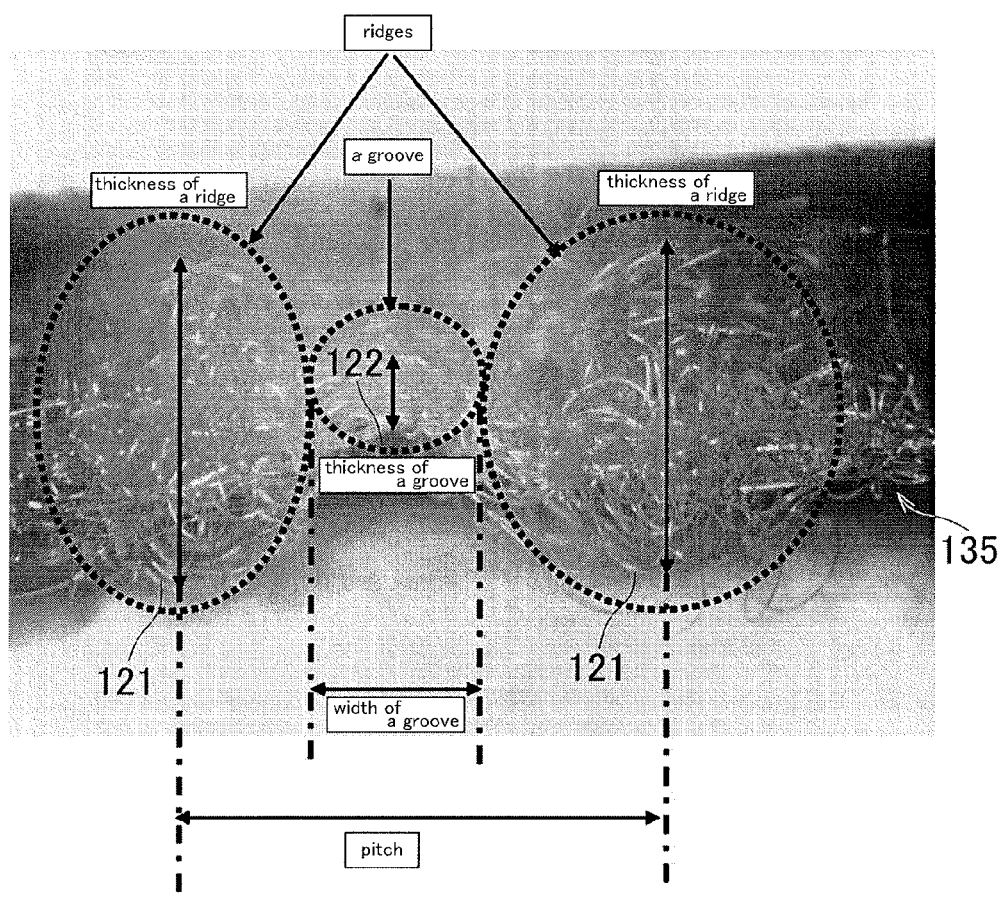
FIG. 9 is a photo of the elastic web in its cross section.

FIG. 9 is a 60-fold magnified photo of a cross section of an example of the elastic web 135 obtained by the process illustrated in FIG. 6. Referring to FIG. 9, the elastic web 135 is formed with the ridges 121 and the grooves 122. The grooves 122 are defined by zones of the web 135 in which the web 135 have come in contact with the apices of the upper teeth 136 or the apices of the lower teeth 137 and the ridges 121 are defined by zones of the web 135 in which the web 135 has been stretched between the upper teeth 136 and the lower teeth 137, and then has contracted again. The ridges 121 are formed of the bundle of the filaments of the inelastic fibers having been permanently deformed and lengthened to sag. The ridges 121 are sufficiently soft and flexible to be easily deformed by light-touching with one's fingertips. Referring to FIG. 9, each of the grooves 122 has a thickness of about 0.3 mm and each of the ridges 121 has a thickness of about 1.2 mm. The ridges 121 are arranged at a pitch of about 2.2 mm.

The inventors have measured surface characteristics of the outer sheets and the elastic sheets attached to these outer sheets in the front and rear waist regions not occupied by the bodily fluid absorbent panel as indices of softness and flexibility of these elastic sheets by using KES-FB4 and obtained measurement result as follows: MIU(-): 0.5 or less; MMD (-): 0.013 or less; and SMD (μm): 5.0 or less. The inventors have measured bending characteristics also of the outer sheets and the elastic sheets attached thereto By using KES-FB2 and obtained measurement result as follows: B(gf*cm²/cm): 0.14 or less; 2 HB(gf*cm/cm); 0.2 or less; and Bwale(gf*cm²/cm): 0.5 or less. Based on these measurement results, the inventors have confirmed that the wearing article characterized in its softness and flexibility can be obtained.

The present invention having been described above on the basis of the pants-type disposable diaper 1 as an embodiment is applicable also to various types of disposable wearing articles such as open-type disposable diapers, pants for incontinent patients and toilet-training pants.

The invention claimed is:

1. A disposable wearing article comprising a front waist region, a rear waist region and a crotch region, each having an inner surface facing a wearer's skin and an outer surface facing a wearer's garment,
   wherein
      the front and rear waist regions are elastically contractible in a waist circumferential direction and
      the inner surfaces of the front and rear waist regions are at least partially formed of elastically contractible elastic sheets,
   wherein:
      the elastic sheets are formed of a mixture of elastically stretchable elastic fibers and inelastically stretchable inelastic fibers;
      ridges and grooves being convex and concave with respect to the wearer's skin are formed of the elastic fibers and the inelastic fibers;
      the ridges and the grooves extend in a vertical direction of the wearing article and arranged alternately in a waist circumferential direction; and
      the elastic sheets have a thickness in the ridges repetitively reduced and restored as the elastic sheets repeat elastic stretch and contraction in the waist circumferential direction.

2. The wearing article defined by claim 1, further comprising: a bodily fluid absorbent panel extending across the crotch region further into the front and rear waist regions,
   wherein the elastic sheet of the rear waist region covers an end of the panel from the inner side of the wearing article and extends in the waist circumferential direction.

3. The wearing article defined by claim 2, wherein the elastic sheet of the front waist region is covered by another end of the bodily fluid absorbent panel from the inner side of the wearing article and extends in the waist circumferential direction.

4. The wearing article defined by claim 1, further comprising an outer sheet at least partially defining the outer surface of the wearing article,
   wherein
      the elastic sheet of the front waist region or the rear waist region has an outer surface attached to said outer sheet from an inner side of the wearing article,
      the outer sheet is formed of a nonwoven fabric made of inelastically stretchable fibers, and
      the outer sheet is formed with gathers undulating in the waist circumferential direction.

5. The wearing article defined by claim 4, wherein the outer sheet comprises the inelastically stretchable fibers in a crimped state.

6. The wearing article defined by claim 4, wherein said outer sheet is directly attached to the outer surface of the elastic sheet at the ridges and the grooves.

7. The wearing article defined by claim 6, wherein the ridges of the elastic sheets of the front and rear waist regions are configured to be in direct contact with the wearer's skin.

8. The wearing article defined by claim 1, wherein:
   each of the elastic sheets is formed of a spun bonded nonwoven fabric having a mass per unit area in a range of 20 to 50 g/m²,
   the elastic fibers comprise polyurethane filaments having a fineness in a range of 2 to 6 dtex,
   the inelastic fibers comprise at least one of polyolefin filaments, polyester filaments and polyamide filaments having a fineness in a range of 2 to 6 dtex, and
   the elastic fibers and the inelastic fibers are mixed at a mass ratio in a range of 40:60 to 60:40.

9. The wearing article defined by claim 1, wherein
   the wearing article is of pants-type,
   respective lateral edges of the front and rear waist regions are joined together at a series of joining portions extending along the lateral edges, and
   the joining portions each has an area of 1 mm² or less.

10. The wearing article defined by claim 1,
    wherein the elastic sheets are rectangles extending in the waist circumferential direction of the article, and a dimension of the elastic sheets in a vertical direction of the article is less than a dimension of each of the front and rear waist regions in the vertical direction,
    wherein the elastic sheets are positioned in middle zones of the front and rear waist regions in the vertical direction.

11. The wearing article defined by claim 1, wherein the ridges of the elastic sheets of the front and rear waist regions are configured to be in direct contact with the wearer's skin.

12. The wearing article defined by claim 1, wherein a thickness of the elastic sheets at the ridges is greater than that at the grooves.

* * * * *